United States Patent [19]

Takeuchi et al.

[11] Patent Number: 5,198,363

[45] Date of Patent: Mar. 30, 1993

[54] DESMUTAGENIC SUBSTANCES AND THEIR PRODUCTION PROCESS

[75] Inventors: Masayasu Takeuchi, Shizuoka; Saburo Kawamura, Tokyo; Taizo Miwa, Kanagawa Ken; Tsuneo Kada, Tokyo, all of Japan

[73] Assignee: Nihon Shokuhin Kako Co., Ltd., Tokyo, Japan

[21] Appl. No.: 393,110

[22] Filed: Aug. 4, 1989

Related U.S. Application Data

[63] Continuation of Ser. No. 828,489, Feb. 12, 1986, abandoned.

[30] Foreign Application Priority Data

Feb. 16, 1985 [JP] Japan .................................. 60-28918

[51] Int. Cl.$^5$ .............................................. C12S 3/04
[52] U.S. Cl. ...................................... 435/277; 426/28; 426/31
[58] Field of Search ................... 435/277; 426/18, 28, 426/31, 49; 127/34; 514/57

[56] References Cited

U.S. PATENT DOCUMENTS

| | | | |
|---|---|---|---|
| 4,181,747 | 1/1980 | Kickle et al. | 426/615 |
| 4,307,121 | 12/1981 | Thompson | 426/431 |
| 4,619,831 | 10/1986 | Sharma | 426/93 |

FOREIGN PATENT DOCUMENTS

| | | |
|---|---|---|
| 0117044 | 8/1984 | European Pat. Off. |
| 0166824 | 1/1986 | European Pat. Off. |

OTHER PUBLICATIONS

Van Soest, P. J. et al., "use of Detergents in the Analysis of Fibrous Feeds. IV. Determination of Plant Cell-Wall Constituents", Journal of the A.O.A.C., vol. 50, No. 1 (1967), pp. 50–55.

Kankyo Heni-gun Kenkyu (Research on Environmental Mutagens), vol. 6, Nos. 1 and 2, published Nov. 30, 1984 by Nippon Kankyo Hen-i Gakkai (Japan Environment Mutation Society), pp. 49–55.

Kada, T. et al., "Absorption of Pyrolysate Mutagens by Vegetable Fibers", Mutation Research, 141 (1984), pp. 140–152.

Ames, B. N. et al.: Mutation Res. (1975) vol. 31, pp. 347–363 "Methods for Detecting Carcinogens and Mutagens With the Salmonella/Mammalian-Microsome Mutagenicity Test".

McCann, J. et al.; Proc. Nat'l Acad. Sci (USA) 1975, vol. 72, pp. 5135–5139 "Detection of Carcinogens as Mutagens in the Salmonella/Microsome Test: Assay of 300 Chemicals".

Matsukura, N. et al.; Science, vol. 213, Jul. 17, 1981, pp. 346–347, "Carinogenicity in Mice of Mutagenic Compounds from a Tryptophan Pyrolyzate".

Ohgaki, H. et al.; Carcinogenesis (1984), vol. 5, No. 6, pp. 815–519, "Carcinogenicity in Mice of Mutagenic Compounds from Glutamic Acid and Soybean Globulin Pyrolysates".

Hackh's Chemical Dictionary, Third Edition (1944), p. 338 "Ferulic Acid".

Japanese Patent Abstracts, vol. 6, No. 106, 1982, (C-108) (1984).

Japanese Patent Abstracts, vol. 9, No. 45 (C-268) (1768) 1985.

Wilson, R. B., et al. (1977) Am. J. Clin. Nutr. 30, 176–181.

Freeman, H. J., et al. (1984) Carbinogenesis 5(2), 261–264.

Wilson, et al. (1977) Chem. Abst., 87: 37811n.
Kada, et al. (1985) Chem. Abst., 102: 91223p.
Freeman, et al. (1984) Chem. Abst., 100: 173585F.

*Primary Examiner*—Charles L. Patterson, Jr.
*Attorney, Agent, or Firm*—Beveridge, DeGrandi, Weilacher & Young

[57] ABSTRACT

The desmutagenic substances consist of a fibrous constituent of food which was produced from corn fibers. These substances have a function of inactivating mutagens which occur in our daily life environment, for example, dinitropyrene, pyrolysate mutagens of food or the like. The process for producing these substances comprises the step of subjecting corn fibers to a treatment process to remove starch, protein and other digestable substances therefrom, the treatment process being an enzyme treatment, chemical treatment or physical treatment or a combination thereof.

3 Claims, No Drawings

DESMUTAGENIC SUBSTANCES AND THEIR PRODUCTION PROCESS

This application is a continuation of pending application Ser. No. 06/828,489 filed Feb. 12, 1986 now abandoned.

BACKGROUND OF THE INVENTION

1. Field of the Invention

The present invention relates to desmutagenic substances and their production process. The desmutagenic substances according to the present invention can effectively inactivate mutagens, namely, substances capable of inducing mutation such as nitroallene or pyrolysate mutagens of food.

2. Description of the Prior Art

Recently, as a result of finding of the fact that the mutagen has a high mutual relation with carcinogenesis, studies for the mutagen have been zealously made by researchers in food or related industries. The mutagen, as is well recognized in the art, has a function of inducing mutation when it acts on deoxyribonucleic acid (DNA).

The mutagens or the substances capable of providing such mutagens occur everywhere in our daily life. One of them is an environmental pollutant such as nitroallene or the like, typically dinitropyrene, for example. Another one is a pyrolysate mutagen of food such as amino acid contained therein. The other mutagens include, for example, a browning substance produced during cooking of food, a tar of tobaccos and the like. These substances are generally recognized to be a very strong mutagen or mutagen-providing substance.

Particularly, dinitropyrene which has been recently found to exist in exhaust gas of diesel engines, along with benzopyrene, necessitate taking a counter-measure to inactivate their mutagenicity. This is because, among numerous environmental pollutants, they have the strongest carcinogenicity as a result of their high mutagenicity. It is reported in the literature that dinitropyrene is a remarkably stable substance and, in animal experiments, it can cause a cancer in an amount of about 80 ng/kg.

Hitherto, there were proposed several methods which were considered to be effective in an inactivation of the mutagens described above. For instance, they include:

(1) Use of Vitamin C

This will inactivate a reaction product of cysteine or sorbic acid with a nitrous acid or an insecticide such as captan, i.e., N-trichloromethylthiotetrahydrophthalimide.

(2) Use of Peroxidase

Peroxidases which are naturally occurring in vegetables will inactivate a pyrolysates of tryptophan (Trp-P-1; a kind of pyrolysate mutagens).

(3) Inhibition of a Formation of Carcinogen Intermediates

In the case that a metabolic intermediate of chemical carcinogens has a toxicity, the mutagens will be inactivated if the formation of such intermediate is inhibited or prevented.

(4) Utilization of Scavenging Action

A fibrous material of vegetables can effectively act as a so-called "scavenger". It can adsorb the combustion product of tryptophan, thereby inactivating the mutagens.

(5) Use of Specially Prepared Cotton Products

A specially prepared cotton product having fixed therein copper phthalocyanine trisulfonic acid is used to detect any mutagen in an environment. This cotton product can adsorb benzo (a) pyrene, thereby inactivating the mutagens.

However, these prior art methods are not satisfactory to inactivate the mutagens, because they are frequently accompanied with drawbacks which will be described below. For example, when vitamin C or peroxidases, both occurring in the vegetables, are used for an inactivation purpose, heat applied during cooking will decompose vitamin C and cause inactivation of peroxidases. This means that desmutagenic activity of the vitamin C and peroxidases is lost during cooking in many cases.

Further, an intake of fibrous vegetables such as burdock, cabbage and carrot as a scavenger is practically inappropriate. In fact, it is difficult to eat a large volume of vegetables at each meal or, alternately, to eat a small amount of vegetables at frequent intervals in a day. In any case, insufficient intake of the fibrous vegetables will not result in a satisfactory inactivation of the mutagens such as pyrolysates of tryptophan.

Furthermore, use of copper phthalocyanine trisulfonic acid or similar compounds proposed in the method (5) should be avoided, since they are toxic to a human body. Of course, they are not to be eaten. Finally, it is noted that inactivation of dinitropyrene with a food component or element has not been taught or suggested in the art as yet.

Under these circumstances, it is now desirable to solve the above-discussed problems of the prior art methods and to provide a novel desmutagenic substance which is produced from corn, a naturally occurring substance having no toxicity to the human body, a small amount of which substance is sufficient to inactivate the mutagens, and an inactivation of which substance is not hindered or adversely affected with the application of heat.

SUMMARY OF THE INVENTION

According to the present invention, there is provided a novel desmutagenic substance consisting of a fibrous constituent of food or, briefly, fibrous food which is a product of corn fibres. The fibrous food of the desmutagenic substance contains as its principal component hardly digestible substances which remain after starch, protein or others have been separated from the corn fibers. The term "hardly digestible" used herein is intended to indicate that the substances have no or low digestability. Preferably, the fibrous food has a Neutral Detergent Fiber (NDF) value of 50% or more and a particle size of not larger than 16 meshes. JOURNAL OF THE A.O.A.C., Vol. 50, No. 1, 1967, pp. 50–55, describes a method of measuring the NDF value. The NDF value indicates a total content of cellulose, hemicellulose and lignin.

According to the present invention, there is also provided a new process for the production of desmutagenic substances which comprises subjecting corn fibers as a starting material to an enzyme treatment, chemical treatment or physical treatment or a combination thereof to remove starch, protein or others therefrom, thereby producing a fibrous constituent of food which contains as its principal component hardly digestible substances.

The enzyme treatment of the corn fibers in the production process according to the present invention can be preferably carried out using one or more of amylolytic, proteolytic, lipolytic and cellulolytic enzymes or an enzyme complex.

Further, the chemical treatment of the corn fibers in the present process can be preferably carried out using an aqueous solution of alkali or acid or, alternatively, with the addition of a surface active agent.

Furthermore, the physical treatment of the corn fibers can be preferably performed using a grinding machine and a sifting machine.

As will be apparent from the below-described preferred embodiments of the present invention and the appended working examples, the desmutagenic substances of the present invention, even though they are used in a very small quantity, can show a remarkably strong desmutagenic action against a variety of mutagens such as dinitropyrene, pyrolysate mutagens or the like. Surprisingly, the desmutagenic action of the desmutagenic substances is not hindered even if they are exposed to heat. In addition, these desmutagenic substances present no toxicity problems to the human body, because they are a product of corn, a naturally occurring food substance. These substances may also exhibit a preventive effect on cancer, which effect is considered to be a result based on their low digestability and short transition time in the human body. In this connection, it is also considered that an injurious action of the mutagens on the body may be completely blocked by the above characteristics of the present desmutagenic substances.

DESCRIPTION OF THE PREFERRED EMBODIMENTS

In the practice of the present invention, corn fibers are used as a starting material. The term "corn fibers" has a meaning generally applied thereto, and indicates a hull or shell portion of corn (Zea mays L.). The corn fibers can be conveniently separated from the corns using a dry milling process or a wet milling process, both of them are conventional. The dry milling process comprises crushing the corns under dry conditions, while the wet milling comprises dipping the corns in a solution of sulfurous acid, milling the wetted corns and sifting the milled corns to separate hulls therefrom.

The corn fibers are treated to remove starch, protein or other unnecessary components therefrom. As a treating process for this purpose, an enzyme treatment, a chemical treatment or a physical treatment may be used separately or in combination. As a result of this treatment, a fibrous constituent of food or fibrous food which contains as its principal component hardly digestible or indigestible substances such as cellulose, hemicellulose or similar substances is produced. The resulting fibrous constituent of food constitutes a desmutagenic substance of the present invention.

As described above, one of the useful treatment processes is an enzyme treatment. The enzyme treatment comprises adding to the corn fibers one or more of amylolytic enzymes, proteolytic enzymes, lipolytic enzymes and cellulolytic enzymes at a pH value of about 3 to 9 and at a temperature of about 30° to 100° C. Typical examples of useful enzymes are described hereinbelow, but the present invention is not limited to these enzymes: The amylolytic enzymes include α-amylase, glucoamylase or the like, the proteolytic enzymes include protease or the like, the lipolytic enzymes include lipase or the like, and the cellulolytic enzymes include cellulase or the like. If desired, a combination of enzymes or an enzyme complex enzyme which can concurrently contain each of the amylolytic enzyme, proteolytic enzyme and lipolytic enzyme, for example, pancreatin, can be used in the present treatment process.

As an alternative, the corn fibers can be chemically treated with an aqueous solution of alkali or acid, or with the addition of a surface active agent. Typical examples of alkali usable in this treatment include sodium hydroxide, potassium hydroxide, calcium hydroxide, sodium carbonate or the like. Useful acids include both of mineral acids such as hydrochloric acid, sulfuric acid, phosphoric acid or the like, and organic acids such as acetic acid, lactic acid or the like, for example. Further, useful surface active agents include, for example, monoglyceride, sugar ester, sodium lauryl sulfate or the like.

Moreover, the corn fibres can be physically treated using a conventional manner and machine. For instance, they can be pulverized with a grinding machine such as a homogenizer or a hammer mill, and then sifted using a sieve with appropriate openings to remove easily crushed starch, protein or similar materials.

We found that an desmutagenic activity of the desmutagenic substances according to the present invention is more increased with increase of surface area of the substances. It is, therefore, desirable that the present desmutagenic substances have a particle size of not larger than 16 meshes. The particle size exceeding 16 meshes should be avoided, because the substances having such large particle size exhibit insufficient desmutagenic activity as a result of decrease of the surface area, and, in addition to this, they are not smoothly passed through the esophagus after they are eaten. The latter means an inferior and unacceptable sense or feeling of eating.

In addition to the particle size of the desmutagenic substances, a Neutral Detergent Fibre (NDF) value of the fibrous constituent of food in said substances is also important, and is preferably 50% or more in terms of anhydride. This is because, in order to inhibit a function of the mutagens in the human body, namely, in order to discharge the mutagens out of the body, it is preferred to control the amount of digestible substances such as starch and protein to a level as low as possible.

From our studies for the present desmutagenic substances up to date, it is believed that an inactivation of the mutagens according to the present invention largely depends on the existence in particular of the hardly digestible substances in the corn fibers, for example, hemicellulose, lignin, inositol, phosphorus compounds, metals or others in addition to cellulose, and therefore a satisfactory inactivation of the mutagens can be attained even with the use of a very small amount of the present substances, if these substances contain a large amount of the hardly digestible substances and they are finely divided to provide a large surface area.

The thus resulting desmutagenic substances of the present invention can be eaten by themselves and, as previously described, a very small amount of them is sufficient to attain the intended purpose. Therefore, these substances can be widely used alone or, alternatively, as a constituent element in the production of the generally used processed foods, health foods, medicines or similar products.

In the practice of the present invention, a desmutagenic activity to the mutagens provided by the desmutagenic substances can be evaluated using a conventional mutation test, for example, Ames's method described on pages 56 to 67 of "An Experimental Method for Environmental Mutagens" published by KODAN-SHA LTD., Tokyo, in 1980. The Ames's method will be briefly described hereinafter.

The mutation test based on the Ames's method has another name: Salmonella test. This test comprises the steps of disseminate a strain of Salmonella having histidine requirement in an agar medium containing only a notably small amount of histidine and then counting the numbers of the growing colonies to determine a mutation rate or level of mutation.

More particularly, the above mutation test can be performed as follows. Assuming that the mutagen in question is dinitropyrene, 5 to 200 mg of the desmutagenic substance of the present invention is added to 1 ml of an aqueous solution of dinitropyrene which concentration is, for example, 0.1 μg/ml, and then left to stand at a room temperature for 1 to 3 hours. Thereafter, the mixture is centrifuged to separate only a supernatant. A predetermined amount (for example, 20 μl) of the supernatant is added to 3 ml of soft agar. The resulting soft agar medium is then used in the Ames's method-based mutation test, after a strain having histidine requirement, for example, Salmonella TA-98 strains, is added to the agar medium. Percentage (%) inactivation of the mutagens can be calculated from the following equation:

$$\% \text{ inactivation} = \frac{(A - B)}{A} \times 100$$

in which

A is a colony count for the mutants formed when an aqueous solution of dinitropyrene which was not previously treated with the present desmutagenic substance was added to the agar medium, and B is a colony count for the mutants formed when an aqueous solution of dinitropyrene previously treated with the present desmutagenic substance was added to the medium.

For this experiment, in order to provide the same environment conditions as in vivo of the animals, a liquid preparation extracted from the liver of rat or rabbit, for example, so-called "S-9 Mix", may be added to the soft agar medium.

The following examples are included to further understand the present invention.

EXAMPLE 1

Corns were crushed with a hammer mill to separate hull portions. The hulls were washed in water, gathered using a wire gauze of 12 meshes, hydro-extracted and dried in air. After drying, the hulls were milled to a particle size of not larger than 32 mesh. A sample with an NDF value of 60% was obtained.

A hundred (100) mg of the sample was added to 1 ml of an aqueous solution of dinitropyrene (0.1 μg/ml), and the mixture was then left to stand for 3 hours. Thereafter, the mixture was centrifuged to separate its supernatant liquid. 20 μl of the separated supernatant was added to a soft agar which was then used in the Ames's method-based mutation test. The test was performed using Salmonella TA-98 strains with histidine requirement. The percentage inactivation of 89.1% resulted.

EXAMPLE 2

Corns were wet-milled in accordance with a conventional manner, and the resulting suspension of corn fibres was treated using a high speed homogenizer. The corn fibres were recovered through a sieve of 32 mesh, washed with a fresh warm water, and then dried in a drafting air at 60° C. The corn fibers were further finely divided using a pulverizer, until the corn fibers having a particle size of not larger than 200 mesh become 90% or more of the total amount. A sample with an NDF value of 88% was obtained.

Thirty (30) mg or 100 mg of the thus obtained sample was each added to 1 ml of an aqueous solution of dinitropyrene (0.1 μg/ml), and the mixture was left to stand at a room temperature for 2 hours. Thereafter, as in the above Example 1, the supernatant liquid was separated, and the mutation test was performed. As a control, the above procedure was repeated without addition of sample to dinitropyrene. The results are shown in the following Table 1.

TABLE 1

| Sample | Number of mutants* | % inactivation |
|---|---|---|
| dinitropyrene (0.1 μg/ml, control) | 2231 | — |
| dinitropyrene (0.1 μg/ml) plus sample (30 mg) | 322 | 85.6 |
| dinitropyrene (0.1 μg/ml) plus sample (100 mg) | 8 | 99.6 |

*Number of mutants was evaluated by subtracting the colony count for the case containing no mutagen from the experimental results.

The above results indicate that the sample substance of the present invention, even though it is used in a small amount such as only 30 mg, can effectively inactivate the mutagenicity of dinitropyrene.

EXAMPLE 3

Corns were first dry-milled. The resulting corn hulls were then roughly milled and passed through a sieve of 20 meshes to recover corn fibers. The corn fibers were then finely divided using a pulverizer to a grain size of not larger than 100 meshes.

Each of 5 mg, 10 mg and 20 mg of the resulting sample was added to 1 ml of 0.1 μg/ml of Glu-p-1 2-amino-6-methyl-dipyrido[1,2-a:3',2'-d]imidazole which is a kind of the pyrolysate mutagens. After being left at a room temperature for 2 hours, the sample was centrifuged and the separated supernatant was filtered through a millipone filter having a pore size of 0.45 micron. The Ames's method-based mutation test was performed using 0.1 ml of the filtrate. In this example, 0.1 ml of a liquid preparation S-9 Mix extracted from the liver of rabbit was added to the soft agar medium. The results are shown in the following Table 2.

TABLE 2

| Sample | Number of mutants* | % inactivation |
|---|---|---|
| Glu-p-1 (0.1 μg/ml, control) | 661 | — |
| Glu-p-1 (0.1 μg/ml) | 243 | 63.2 |

TABLE 2-continued

| Sample | Number of mutants* | % inactivation |
|---|---|---|
| plus sample (5 mg) | | |
| Glu-p-1 (0.1 μg/ml) plus sample (10 mg) | 108 | 83.7 |
| Glu-p-1 (0.1 μg/ml) plus sample (20 mg) | 120 | 81.8 |

*see Table 1

The above results indicate that the sample substance produced from the corn fibers according to the present invention has an excellent desmutagenic activity against the pyrolysate mutagens. This may mean that, when we eat grilled meat which contains pyrolysate mutagens on its surface, we may effectively prevent a formation of carcinomas due to the pyrolysate mutagens, if we concurrently take a very small amount of the sample substance produced from corn fibers according to the invention.

EXAMPLE 4

Corns were first subjected to a wet milling process. The resulting milling product of corn hulls was slurried, heated to 90° C., and mixed with "KleistaseT-5" (trade name; amylolytic enzyme commercially available from Daiwa Kasei Kogyo Kabushiki Kaisha). After the reaction for 2 hours, the reaction product was then mixed with "BIOPLASE SP" (trade name; proteolytic enzyme commercially available from Nagase & Co., Ltd.), and reacted for further 5 hours. Starch, protein and other digestible substances were removed. The residue was washed with water, recovered, and dried in a drafting air. After the drying was completed, the solid substance was further finely divided, and passed through a sieve of 60 meshes. The resultant powdered sample had an NDF value of 87%.

Each of 5 mg, 10 mg and 20 mg of the powdered sample was added to 1 ml of 1 μg/ml of Trp-p-1,3-amino-1,4-dimethyl-5H-pyrido[4,3-b]indole (a kind of the pyrolysate mutagens). The mixture was left to stand at a room temperature for 2.5 hours. As in Example 1 described above, a supernatant was separated, and 0.1 ml of the supernatant was subjected to the Ames's method based mutation test. In this example, as in the above Example 3, 0.1 ml of a liquid preparation of S-9 Mix was added to the soft agar medium. The results are summarized in the Table 3.

TABLE 3

| Sample | Number of mutants* | % inactivation |
|---|---|---|
| Trp-p-1 (1 μg/ml, control) | 809 | — |
| Trp-p-1 (1 μg/ml) plus sample (5 mg) | 20 | 97.5 |
| Trp-p-1 (1 μg/ml) plus sample (10 mg) | 15 | 98.1 |
| Trp-p-1 (1 μg/ml) plus sample (20 mg) | 34 | 95.8 |

*see Table 1

The above results indicate that the sample substance according to the present invention has a high desmutagenic activity against the pyrolysate mutagen Trp-p-1 and that the satisfactory desmutagenic activity can be attained even with the use of a very small amount of the substance of the present invention.

What is claimed is:

1. A non-toxic desmutagenic substance not adversely affected by application of heat in cooking consisting of a fibrous constituent of food having a Neutral Detergent Fiber (NDF) value of 87% or more and a particle size of not larger than 60 mesh which contains as its principal component hardly digestible substances containing hemicellulose, cellulose and lignin which remain after subjecting corn fibers to a combination of both an enzyme treatment and physical treatment thereof, wherein the enzyme treatment uses one or more of amylolytic, proteolytic, lipolytic and cellulolytic enzymes or an enzyme complex, whereby starch, protein and other digestibles are separated from the corn fibers.

2. A process for the production of non-toxic desmutagenic substances not adversely affected by application of heat in cooking which comprises subjecting corn fibers to a combination of both an enzyme treatment and physical treatment thereof, wherein the enzyme treatment uses one or more of amylolytic, proteolytic, lipolytic and cellulolytic enzymes or an enzyme complex and the physical treatment uses a grinding machine and a sifting machine, thereby producing a fibrous constituent of food having a Neutral Detergent Fiber (NDF) value of 87% or more and a particle size of not larger than 60 mesh.

3. A non-toxic desmutagenic substance not adversely affected by application of heat in cooking consisting of a fibrous constituent of food having a Neutral Detergent Fiber (NDF) value of 87% or more and a particle size of not larger than 60 mesh which contains as its principal component hardly digestible substances containing hemicellulose, cellulose and lignin, and which has been produced from corn fibers in a process as claimed in claim 2.

* * * * *